(12) United States Patent
Barry et al.

(10) Patent No.: US 6,896,120 B2
(45) Date of Patent: May 24, 2005

(54) PASSIVE TRANSFER GUIDE FOR CONVEYOR TRACK

(75) Inventors: Douglas Barry, Lincoln, NE (US); Don R. Simms, Council Bluffs, IA (US); Inna M. Zevakina, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 123 days.

(21) Appl. No.: 10/627,341

(22) Filed: Jul. 25, 2003

(65) Prior Publication Data

US 2005/0023109 A1 Feb. 3, 2005

Related U.S. Application Data

(60) Provisional application No. 60/398,893, filed on Jul. 26, 2002.

(51) Int. Cl.[7] .............................................. B65G 47/74
(52) U.S. Cl. .................. 198/367; 198/636; 198/457.05; 198/594; 198/812
(58) Field of Search ............................. 198/367, 367.1, 198/457.05, 594, 636, 637, 812

(56) References Cited

U.S. PATENT DOCUMENTS

| | | | | |
|---|---|---|---|---|
| 1,726,657 A | * | 9/1929 | Ekvall | |
| 1,733,409 A | * | 10/1929 | Howe | |
| 2,078,236 A | * | 4/1937 | Chapman | |
| 2,168,191 A | * | 8/1939 | Bergmann | |
| 2,346,583 A | * | 4/1944 | Jackson | |
| 2,363,920 A | * | 11/1944 | Young et al. | |
| 2,465,690 A | * | 3/1949 | Lyon | |
| 2,986,261 A | * | 5/1961 | Wenstrand | |
| 3,160,259 A | * | 12/1964 | Dalton | |
| 3,701,407 A | * | 10/1972 | Kulig | 198/457.05 |
| 3,721,331 A | * | 3/1973 | Holbrook et al. | 198/367 |
| 3,960,266 A | * | 6/1976 | Becker | 198/430 |
| 4,413,724 A | * | 11/1983 | Fellner | 198/594 |
| 4,549,647 A | * | 10/1985 | Cosse | 198/461.1 |
| 4,690,266 A | * | 9/1987 | Croman et al. | 198/388 |
| 5,088,589 A | * | 2/1992 | Geerts | 198/457.05 |
| 5,228,551 A | * | 7/1993 | Kluttermann et al. | 198/468.11 |
| 5,634,550 A | * | 6/1997 | Ensch et al. | 198/457.05 |
| 5,772,005 A | * | 6/1998 | Hansch | 198/594 |
| 6,202,829 B1 | * | 3/2001 | van Dyke et al. | 198/465.2 |
| 6,241,074 B1 | * | 6/2001 | Steeber | 198/456 |
| 6,478,144 B1 | * | 11/2002 | Sweazy | 198/890 |

* cited by examiner

Primary Examiner—Douglas Hess

(57) ABSTRACT

The passive transfer guide of the present invention is positioned in a section of tangency between a first continuous loop conveyor and a second continuous loop conveyor, with a first guide lane for directing a specimen carrier from the first conveyor to the second conveyor, and a second guide lane for directing a specimen carrier from the second conveyor to the first conveyor. The guide includes a horizontally oriented "H"-shaped central member having a pair of upper legs, a pair of lower legs, and a cross-member connecting the upper and lower legs. The upper legs and an upper portion of the cross-member form one specimen carrier-directing lane, and the lower legs and a lower portion of the cross-member form the second carrier-directing lane.

19 Claims, 3 Drawing Sheets

PASSIVE TRANSFER GUIDE FOR CONVEYOR TRACK

CROSS-REFERENCES TO RELATED APPLICATIONS

This application claims the benefit of U.S. Provisional Application Ser. No. 60/398,893, filed Jul. 26, 2002.

STATEMENT AS TO RIGHTS TO INVENTIONS MADE UNDER FEDERALLY SPONSORED RESEARCH AND DEVELOPMENT (Not applicable)

BACKGROUND OF THE INVENTION (1) Field of the Invention

The present invention relates generally to track utilized in an automated clinical laboratory conveyor system, and more particularly to an improved guide apparatus for transferring specimen carriers from one track loop to another.

(2) Background Information

Clinical laboratory testing has changed and improved remarkably over the past 80 years. Initially, tests or assays were performed manually and generally utilized large quantities of serum, blood or other materials and/or body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of physical specimen required to perform a particular test.

Instruments have been developed to increase the efficiency of testing procedures by reducing turnaround time and decreasing the volumes necessary to perform various assays. Robotic engineering has evolved to such a degree that various types of robots have been applied in the clinical laboratory setting.

The main focus of prior art laboratory automation relied on the implementation of conveyor systems to connect areas of a clinical laboratory. Known conveyor systems in the laboratory setting utilize separate conveyor segments to move specimens from a processing station to a specific laboratory work station. In order to obtain cost savings, one typical scenario called for specimens to be sorted manually and grouped together in a carrier rack to be conveyed to a specific location. In this way, a carrier would move a group of 5–20 specimens from the processing location to the specific work station for the performance of a single test on each of the specimens within the carrier rack.

With the development of new and improved automatic conveyor systems for laboratories and other environments, it is possible to select, track, and convey individual specimens throughout a laboratory for a variety of different testing, while maintaining a priority system for certain types of testing or special urgent requests for a time-specific response. These new automated conveyor systems are of various types and design, but the inventors herein have found that a dual conveyor system, using a pair of parallel conveyor tracks circulating throughout a laboratory, provides the greatest flexibility and versatility. The integration of various track devices with software directing the operation of the conveyor system and the various automated testing stations, has improved both the speed and capability of automated conveyor systems in recent years.

Track devices form the physical interface between the specimen samples in carriers being directed throughout the system, while the Laboratory Automation System (LAS) database provides direction for the system through its command and control features. The LAS and the various track devices work in combination to direct, manage and track all specimens throughout the system.

The dual-lane conveyors used with the present invention utilize table top chain to transport specimen carriers about a closed loop among various stations. There are several limits in the use of table top chain as the conveyor in an automated laboratory setting. While the total amount of linear feet capable of being driven by a single motor is typically sufficient for most laboratory settings, a track loop cannot contain more than 720° of angles in aggregate. A simple rectangular shape with two 180° corners utilizes a total of 360° of aggregate angles in a single loop. Similarly, a loop formed in the shape of an "L" utilizes 540° of aggregate angle, while a "U"-shaped track uses the maximum aggregate of angles, totaling 720°.

An advantage of a dual track conveyor is the possibility of running the two tracks at different speeds. This permits a specimen to be moved to a "fast track" between various job sites, and to the slower track when awaiting the performance of a desired task. However, with the limitations of the aggregate angles, there is a limit to the flexibility and capacity of a single loop system, even with dual tracks in the loop.

BRIEF SUMMARY OF THE INVENTION

It is therefore a general object of the present invention to provide an improved passive transfer guide for moving specimen carriers from one closed loop system to another in an automated conveyor system.

These and other objects will be apparent to those skilled in the art.

The passive transfer guide of the present invention is positioned in a section of tangency between a first continuous loop conveyor and a second continuous loop conveyor, with a first guide lane for directing a specimen carrier from the first conveyor to the second conveyor, and a second guide lane for directing a specimen carrier from the second conveyor to the first conveyor. The guide includes a horizontally oriented "H"-shaped central member having a pair of upper legs, a pair of lower legs, and a cross-member connecting the upper and lower legs. The upper legs and an upper portion of the cross-member form one specimen carrier-directing lane, and the lower legs and a lower portion of the cross-member form the second carrier-directing lane.

BRIEF DESCRIPTION OF THE SEVERAL VIEWS OF THE DRAWING

The preferred embodiment of the invention is illustrated in the accompanying drawings, in which similar or corresponding parts are identified with the same reference numeral throughout the several views, and in which.

DETAILED DESCRIPTION OF THE INVENTION

Figure 1:
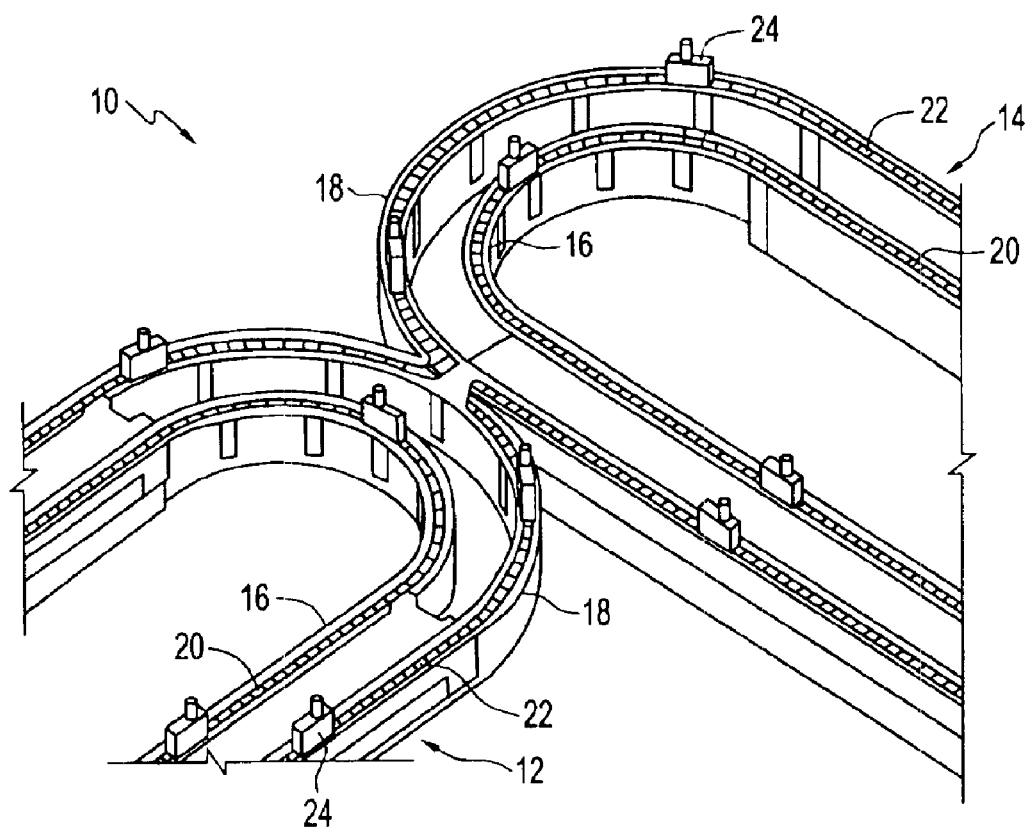
FIG. 1 is a perspective view of a passive transfer guide of the present invention installed between a pair of conveyor track loops.

Referring now to the drawings, in which similar or corresponding parts are identified with the same reference numeral, and more particularly to FIG. 1, the passive transfer guide of the present invention is designated generally at 10, and is shown installed between two loops of track 12 and 14 of an automated conveyor transport system.

Each loop 12 and 14 is a continuous loop, dual-lane track having integrated continuous loop conveyors 16 and 18 forming an inside lane 20 and an outside lane 22, respectively for transporting specimens within specimen carriers 24. Each loop 12 and 14 is supported above the ground by support frames (not shown) spaced along the track where needed.

Figure 2:
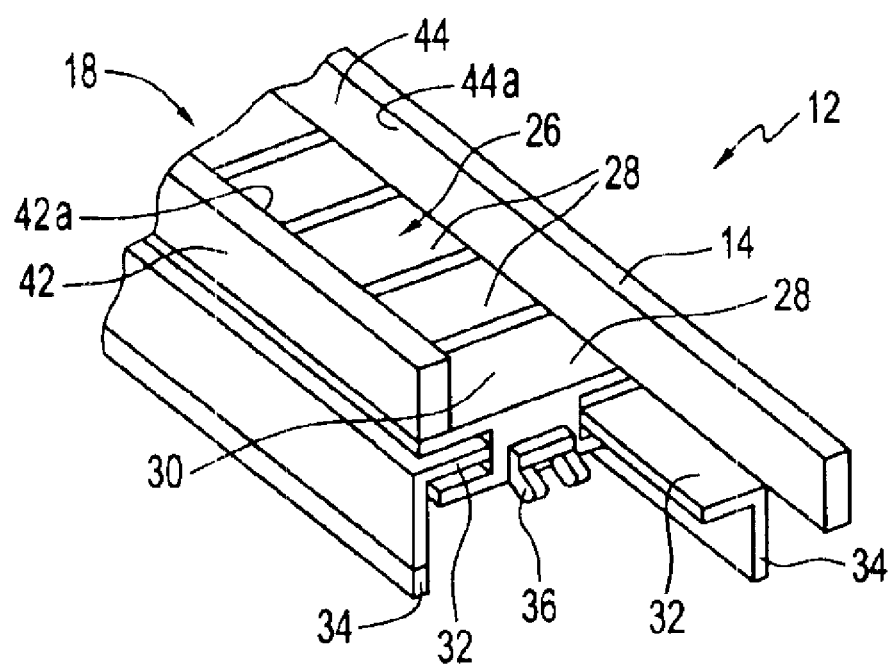
FIG. 2 is an enlarged cutaway perspective of a portion of the conveyor track.

Referring now to FIG. 2, one lane 22 of track 12 is cutaway to show the construction of the conveyor 18 and track 12 in more detail. Conveyor 18 uses a table top chain 26, known in the art, and includes a plurality of plates 28, each having a flat upper surface 30 (or "table top") and a generally "H"-shaped cross-section. A leg 32 of an elongated extrusion 34 projects within each of the notches of the "H" of plates 28, to guide the plates as they are moved. Plates 28 are interconnected by links 36, which permit the plates 28 to pivot about the links 36 within a horizontal plane. The links 36 are engaged by a drive mechanism to pull the chain along the guide extrusions 34 and thereby drive the chain 26. The upper surfaces 30 of plates 28 form a flat planar surface that will transport specimen carriers 24.

A pair of elongated guide rails 42 and 44 are disposed along the lengths of conveyor 18 on opposing sides of the plates 28 to guide the specimen carriers 24 therebetween. Preferably, guide rails 42 and 44 are space above extrusions 34 and generally parallel thereto, with smooth vertical surfaces 42a and 44a oriented inwardly towards the plates, against which the sides of the specimen carriers 24 will contact as they are transported on plates 28.

Figure 3:
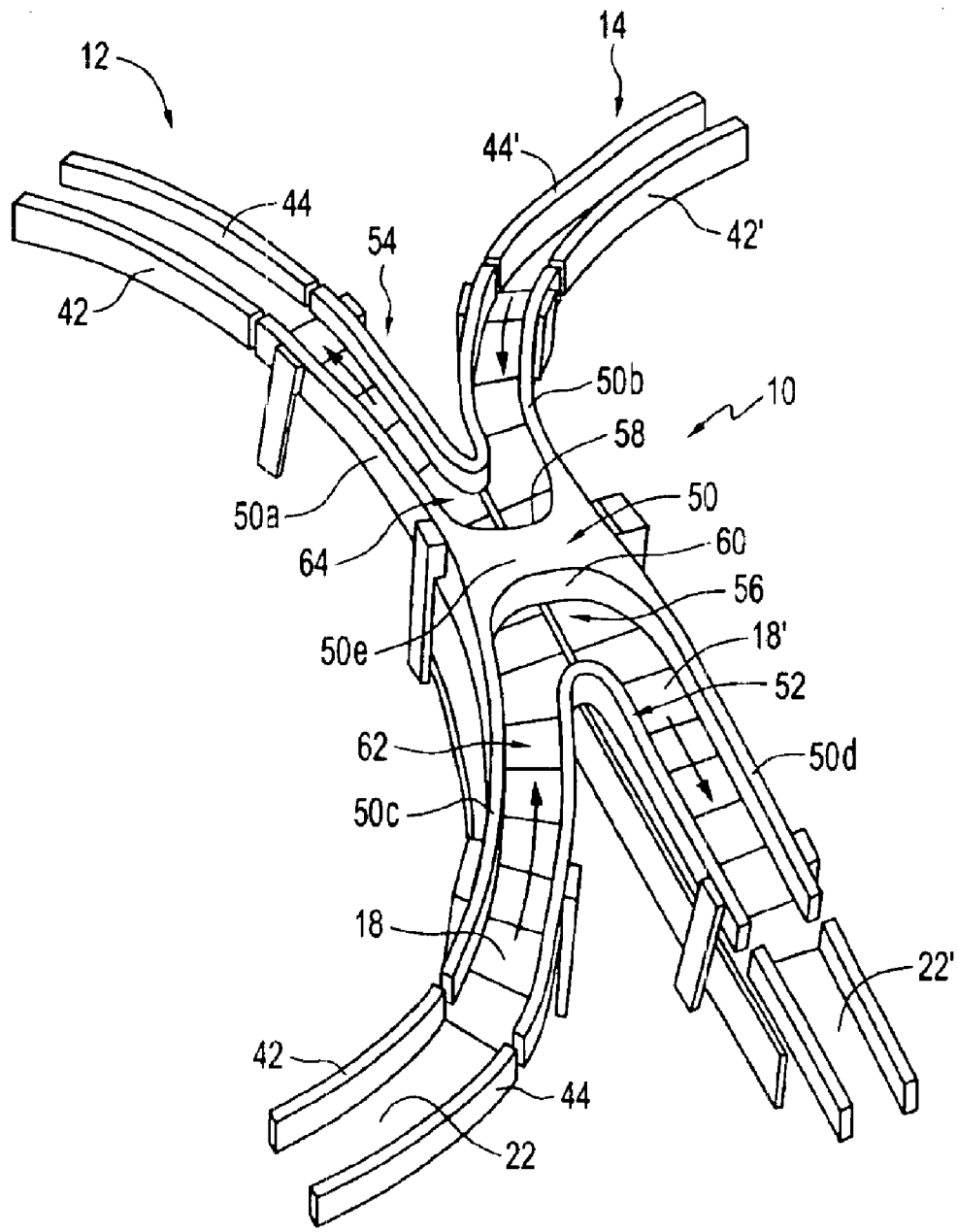
FIG. 3 is an enlarged perspective view of the passive transfer guide.

Referring now to FIG. 3, passive transfer guide 10 is positioned between loops 12 and 14 and interconnects the outer lane 22 of loop 12 with the outer lane 22' of loop 14. While the passive transfer guide 10 will in most cases be located at the curves of two adjacent loops 12 and 14, it should be noted that the guide 10 may be used in any location where the outer lanes 22 and 22' are adjacent one another with the associated conveyors 18 and 18' traveling in opposite directions. For purposes of clarity, guide rail 42 of loop 12 and guide rail 42' of loop 14 will be denoted the inward guide rails, while the opposing rails 44 and 44' will be denoted the outward guide rails.

Passive transfer guide 10 consists of three general parts: a central member 50 and two inserts 52 and 54. Central member 50 is a generally "H"-shaped plastic piece having two upper legs 50a and 50b, two lower legs 50c and 50d, and a central cross-member 50e. The inward and outward guide rails 42, 42', 44 and 44' of a portion of loops 12 and 14 are removed at the section of tangency, designated generally at 56, of the conveyors 18 and 18'. These removed guide rails are replaced with the guide 10 as described below.

Upper leg 50a and lower leg 50c of central member 50 are aligned and positioned to continue the inward guide rail 42 of loop 12. Upper leg 50b and lower leg 50d of central member 50 are aligned and positioned to continue the inward guide rail 42' of loop 14. Cross-member 50e has a smooth, arcuate "U"-shaped arch 58 forming the vertical surface extending between the inward surfaces of upper legs 50a and 50b. Thus, legs 50a and 50b and cross-member arch 58 form a smooth continuous contact surface for a specimen carrier to follow as it travels through the upper portion of guide 10. Similarly, a smooth, arcuate inverted "U"-shaped arch 60 is formed on the vertical surface of cross-member 50e extending between the inward surfaces of lower legs 50c and 50d. In this way, legs 50c and 50d and cross-member arch 60 form a smooth continuous contact surface for a specimen carrier to follow as it travels through the lower portion of guide 10.

Conveyors 18 and 18' are coplanar at the section of tangency 56, so that conveyor 18 will push a specimen carrier 24 into the curved surface of lower arch 60, turning the carrier off of conveyor 18 and on to conveyor 18', moving in the opposite direction. Conveyor 18' will then pull the carrier on through the lower portion of guide 10 and fully onto conveyor 18'. Similar movement occurs in the upper portion of guide 10 along arch 58, from conveyor 18' to conveyor 18.

Insert 52 includes an inverted "V"-shaped guide rail with one leg 52a positioned to continue the lower of the outward guide rails 44 of loop 12, and the other leg 52b positioned to continue the adjacent lower outward guide rail 44' of loop 14. In this way insert 52 and the lower portion of central member 50 form a slot or transfer lane 62 through which a specimen carrier 24 will pass and be guided. Insert 54 includes a "V"-shaped guide rail with one leg 54a positioned to continue the upper of the outward guide rails 44 of loop 12, and the other leg 54b positioned to continue the adjacent upper outward guide rail 44' of loop 14. In this way insert 54 and the upper portion of central member 50 form a slot or transfer lane 64 through which a specimen carrier 24 will pass and be guided.

Guide 10 is passive in that it does not move in order to transfer a specimen carrier 24 from one loop to another. Rather, it is the movement of the conveyors 18 and 18' that actually cause the transfer to occur. Thus, guide 10 has no moving parts, making the apparatus a virtually maintenance-free device.

Whereas the invention has been shown and described in connection with the preferred embodiment thereof, many modifications, substitutions and additions may be made which are within the intended broad scope of the appended claims.

What is claimed is:

1. A passive transfer guide for shifting specimen carriers from a first continuous loop conveyor to a second continuous loop conveyor, and back again, comprising:

a generally horizontally oriented "H"-shaped central member having a pair of upper legs, a pair of lower legs, and a cross-member connecting the upper and lower legs;

the upper legs and an upper portion of the cross-member having a smooth continuous vertical surface forming a "U"-shaped horizontally oriented guide rail for directing a specimen carrier therealong; and the lower legs and a lower portion of the cross-member having a smooth continuous vertical surface forming an inverted "U"-shaped horizontally oriented guide rail oriented in an opposite direction to the upper legs.

2. The passive transfer guide of claim 1, wherein said cross-member upper portion has a smooth, arcuate U-shaped arch formed therein interconnecting the upper legs.

3. The passive transfer guide of claim 1, wherein said cross-member lower portion has a smooth, arcuate inverted U-shaped arch formed therein interconnecting the lower legs.

4. The passive transfer guide of claim 1, further comprising an inverted U-shaped insert having a pair of legs extending from a juncture, the insert positioned between the lower legs of the central member to form an inverted U-shaped lane for directing specimen carriers.

5. The passive transfer guide of claim 4, wherein said inverted U-shaped insert and central member are coplanar.

6. The passive transfer guide of claim 5, wherein the legs of said inverted U-shaped insert are substantially parallel to and uniformly spaced apart from the lower legs of the central member.

7. The passive transfer guide of claim 6, further comprising a U-shaped insert having a pair of legs extending from a juncture, the insert positioned between the upper legs of the central member to form a U-shaped lane for directing specimen carriers.

8. The passive transfer guide of claim 7, wherein said U-shaped insert and central member are coplanar.

9. The passive transfer guide of claim 8, wherein the legs of said U-shaped insert are substantially parallel to and uniformly spaced apart from the upper legs of the central member.

10. In combination:
- a first continuous loop track with a first continuous loop conveyor thereon, said first conveyor operably mounted on said track with an upper support surface forming a substantially horizontal drive plane;
- a second continuous loop track with a second continuous loop conveyor thereon, said second conveyor operably mounted on said track with an upper support surface forming a substantially horizontal drive plane;
- said first and second loop conveyors oriented with at least one portion of each loop tangent one another, forming a section of tangency;
- said first and second loops conveyors operable such that the respective conveyors are moving in opposite directions with the drive planes being substantially coplanar at the section of tangency;
- said first loop having a pair of inward and outward spaced apart guide rails above the first conveyor, forming a lane for directing specimen carriers transported on the first conveyor;
- said second loop having a pair of inward and outward spaced apart guide rails above the second conveyor, forming a lane for directing specimen carriers transported on the second conveyor; and
- a passive transfer guide oriented in the section of tangency with a first guide lane for directing a specimen carrier from the first conveyor to the second carrier, and a second guide lane for directing a specimen carrier from the second conveyor to the first conveyor.

11. The combination of claim 10, wherein said passive transfer guide includes:
- a generally horizontally oriented "H"-shaped central member having a pair of upper legs, a pair of lower legs, and a cross-member connecting the upper and lower legs;
- the upper legs and an upper portion of the cross-member having a smooth continuous vertical surface forming a "U"-shaped horizontally oriented guide rail extending from the inward guide rail of the second conveyor, through the section of tangency and thence to the inward guide rail of the first conveyor, for directing a specimen carrier therealong; and
- the lower legs and a lower portion of the cross-member having a smooth continuous vertical surface forming an inverted "U"-shaped horizontally oriented guide rail extending from the inward guide rail of the first conveyor, through the section of tangency and thence to the inward guide rail of the second conveyor, and oriented in an opposite direction to the upper legs.

12. The combination of claim 11, wherein said cross-member upper portion has a smooth, arcuate U-shaped arch formed therein interconnecting the upper legs.

13. The combination of claim 11, wherein said cross-member lower portion has a smooth, arcuate inverted U-shaped arch formed therein interconnecting the lower legs.

14. The combination of claim 11, further comprising an inverted U-shaped insert having a pair of legs extending from a juncture to each of the outward guide rails of the first and second loops, the insert positioned between the lower legs of the central member to form an inverted U-shaped lane for directing specimen carriers.

15. The combination of claim 14, wherein said inverted U-shaped insert and central member are coplanar.

16. The combination of claim 15, wherein the legs of said inverted U-shaped insert are substantially parallel to and uniformly spaced apart from the lower legs of the central member.

17. The combination of claim 16, further comprising a U-shaped insert having a pair of legs extending from a juncture to each of the outward guide rails of the first and second loops, the insert positioned between the upper legs of the central member to form a U-shaped lane for directing specimen carriers.

18. The combination of claim 17, wherein said U-shaped insert and central member are coplanar.

19. The combination of claim 18, wherein the legs of said U-shaped insert are substantially parallel to and uniformly spaced apart from the upper legs of the central member.

* * * * *